United States Patent [19]
Myers et al.

[11] Patent Number: 5,236,359
[45] Date of Patent: Aug. 17, 1993

[54] TAPPING TOOL AND METHOD FOR IMPLANT DENTISTRY

[75] Inventor: James R. Myers, Altamonte Springs, Fla.; John G. Hughes, Winter Park, Fla.

[73] Assignee: R&J Innovations, Inc., Maitland, Fla.

[21] Appl. No.: 835,763

[22] Filed: Feb. 13, 1992

Related U.S. Application Data

[63] Continuation-in-part of Ser. No. 773,156, Oct. 8, 1991, Pat. No. 5,129,823.

[51] Int. Cl.⁵ .......................... A61C 3/02; A61C 3/00; A61C 5/00
[52] U.S. Cl. .................................. 433/144; 433/141; 433/215; 408/128
[58] Field of Search ............... 433/144, 145, 141, 173, 433/215; 408/123, 127, 128

[56] References Cited

U.S. PATENT DOCUMENTS

| | | | |
|---|---|---|---|
| 946,984 | 1/1910 | Parman | 408/128 |
| 960,002 | 5/1910 | Dailey | 408/128 |
| 2,830,479 | 4/1958 | Finn | 81/57.3 |
| 3,283,621 | 11/1966 | Faso | 81/57.3 |
| 3,852,884 | 12/1974 | Lazarus | 433/141 |
| 4,735,119 | 4/1988 | Riley | 81/57.3 |
| 4,799,832 | 1/1989 | Abbott | 408/123 |
| 4,976,617 | 12/1990 | Carchidi | 433/141 |
| 4,995,810 | 2/1991 | Söderberg | 433/141 |
| 5,030,096 | 8/1991 | Hurson et al. | 433/173 |
| 5,129,823 | 7/1992 | Hughes | 433/141 |

FOREIGN PATENT DOCUMENTS 0230326  8/1987  European Pat. Off. ............ 433/147

Primary Examiner—Gene Mancene
Assistant Examiner—Cindy A. Cherichetti
Attorney, Agent, or Firm—Franz, Warren L.

[57] ABSTRACT

A tool for the tapping of a bone hole and installation of an implant in dentistry has a knob manually rotatable externally of a patient's mouth on one end of an arm and a bit, releasably secured on a sprocket, rotatable inside the patient's mouth in response to rotation of the knob. A chain connects the bit sprocket to a sprocket attached to the knob, so that the bit rotates about an axis parallel to, but laterally offset by the arm from, the axis of rotation of the knob. For bone tapping purposes, a tapping bit is used and a "T"-shaped handle attaches to the knob to increase the lever arm for torque application. For screwing implant components together or into the tapped bone, a screwing bit is used. A resilient elastomer sleeve is releasably stretched over the implant component and over the screwing bit for initial positioning. Multiple, interchangeable bits are provided to match different-sized implant components. The shank of each bit is recessed intermediate cylindrical portions, for receiving a set screw.

8 Claims, 2 Drawing Sheets

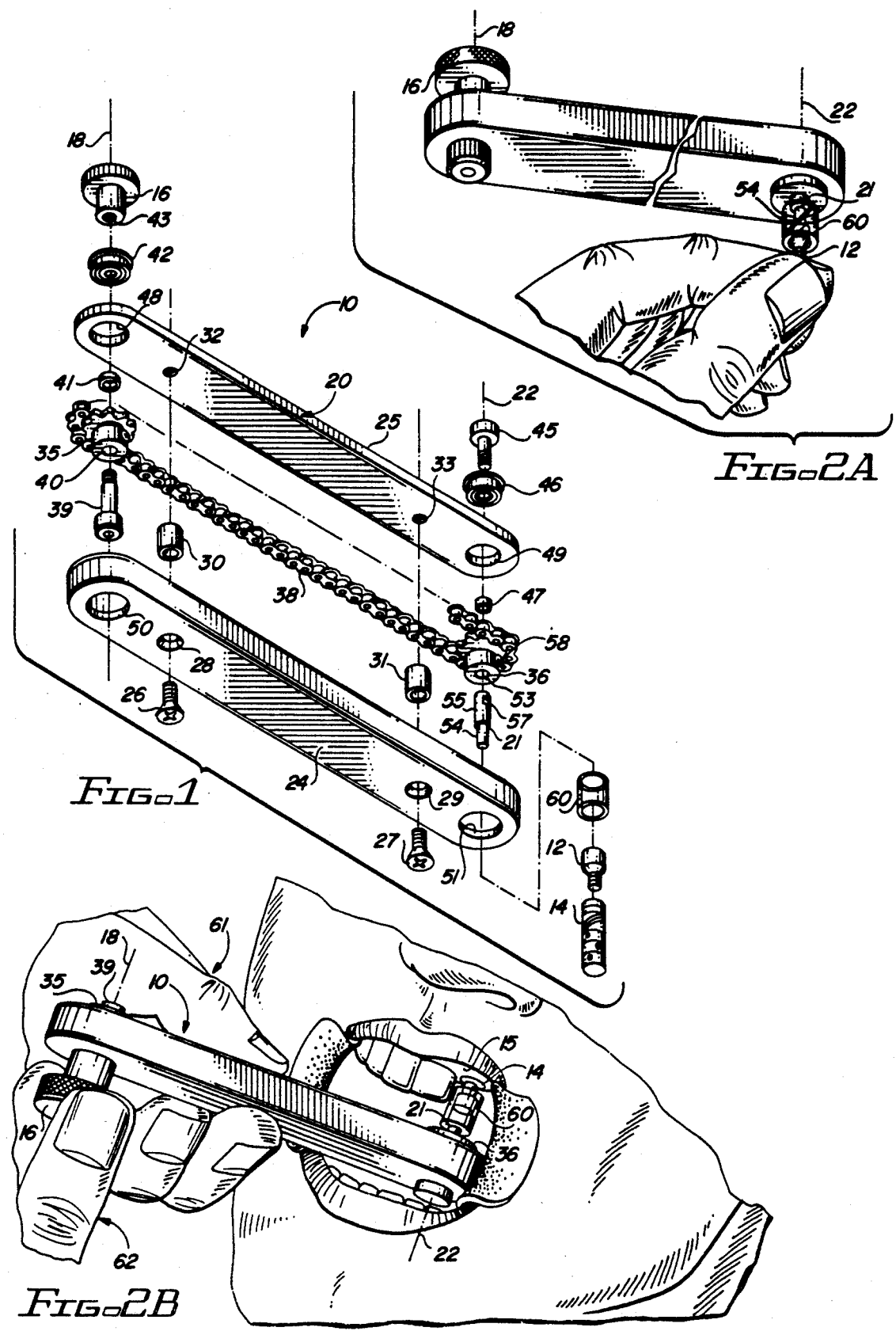

TAPPING TOOL AND METHOD FOR IMPLANT DENTISTRY

This is a continuation-in-part of U.S. patent application Ser. No. 07/773,156 filed Oct. 8, 1991, now U.S. Pat. No. 5,129,823 the disclosure of which is incorporated herein by reference.

BACKGROUND OF THE INVENTION

This invention relates generally to a driver tool and method for installation of implants in dentistry; and, more particularly, to a hand-operated tool having interchangeable bits that can be manipulated within the mouth of the patient by hand movements executed externally.

The installation of implants within the mouth in dentistry is both stressful and hazardous. The mouth has a small opening relative to a dentist's hands, and is a difficult place to work. Implant components are small and difficult to grasp, and great care must be taken that the same are not swallowed or aspirated by the patient.

The tapping or threading of holes drilled in the bone at an implant site, the threading of implant bases into the tapped holes, and the attachment of fasteners onto the implant structure are all conventionally undertaken using small handheld implements which have shanks and handles sized to fit within the mouth, and which are gripped and rotated within the mouth by the dentist's hand. Such tools have the advantage that the tightening action can be "felt" by the dentist, and carefully controlled. They are, however, difficult to manipulate in such close quarters and, if dropped, can become lodged in the patient's throat. Their use, thus, requires much concentration and is exhausting.

The use of ratchet-type wrenches for installation of abutments and screws is known, though the same offer relatively little advantage over the straight shank direct application screwdrivers. The ratchet action offers less control because is interferes with the "feel" or tactile sensitivity of the installation, and the ratcheting movement introduces undesirable instability in a sensitive procedure. (In ratcheting, the dentist is unable to get the desired tactile feedback regarding torque resistance of the meshing threads, etc.) The use of screwdriver bits on electrical dental handpieces is likewise undesirable because of the complete loss of tactile sensitivity with the attendant risk of either breaking the screw or spinning the implant in the bone.

SUMMARY OF THE INVENTION

Commonly-owned, copending patent application Ser. No. 07/773,156 discloses a hand-operated driving tool and a method utilizing that tool for the installation of implant components in dentistry. The tool provides an offset so that bits can be manipulated within the mouth by direct positive drive of hand movements executed outside the mouth.

As described in the '156 application, the tool comprises an offset arrangement including a hand-grippable drive member mounted for manual rotation about a first axis at one end of an elongated structural element, a driver head or the like bit member mounted for rotation about a second axis parallel to the first axis at the other end of the structural element, and torque transmission means connecting the drive member and the bit, so that hand rotation of the drive member about the first axis outside the mouth will cause like rotation of the bit about the second axis within the mouth. This application further defines the tool and method, by clarifying that the tool can be used not only for screwing implant components into each other and into the bone, but also for pretapping the bone to provide internal threading against which outside threading on an implant can be meshed.

In a preferred embodiment of the invention, described in greater detail below, a tool of the type described in the '156 application has a hand-grippable member modified to receive a lever arm assembly in the form of a T-shaped element, includes a bone tapping bit member usable to tap a hole drilled in the mandible or maxilla in order to provide threading against which complementary threading of a threaded implant element can be meshed. A plurality of interchangeable, different-sized tapping bits may be provided to accommodate different-sized bone holes and implant thread sizes, each tapping bit being capable of being selectively, releasably secured to the tool in the same manner as the other bits described in the '156 application. And, as with the other bits, the bone tapping bits are provided with shanks having reduced intermediate portions, against which a set screw can be tightened. Enlargements of the shaft above and below the flat region prevent loss of the bits during use, even if the set screw should become slightly loosened.

The invention provides an apparatus and a method for the tapping of a bone hole, and installation therein of a dental implant, giving the same "feel" and control as conventional hand-held dental bone taps and implant screwdrivers, with greater capability for maneuverability, and with reduced risk of tool or implant part swallowing or aspiration, thereby greatly reducing the anxiety and stress associated with such installation.

BRIEF DESCRIPTION OF THE DRAWINGS

Embodiments of the apparatus and method of the invention have been chosen for purposes of illustration and description, and are shown in the accompanying drawings, wherein:

FIG. 1 is an exploded view of a driver tool in accordance with the invention;

FIGS. 2A-2B are views showing the steps in a method of installing an implant component according to the invention, utilizing the tool of FIG. 1;

Throughout the drawings, like elements are referred to by like numerals.

DETAILED DESCRIPTION OF PREFERRED EMBODIMENTS

Figure 3:
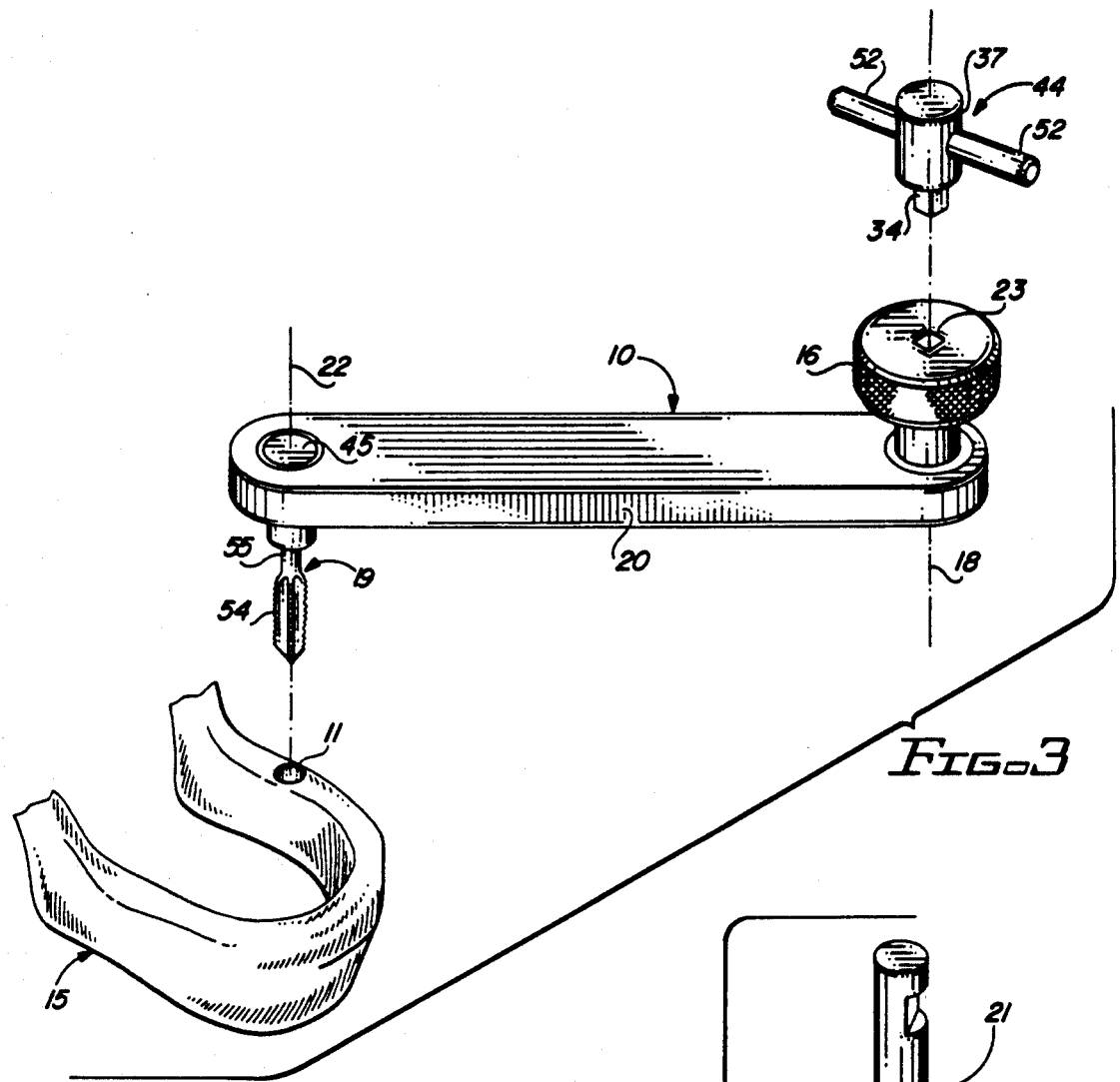
FIG. 3 is a view of the tool of FIG. 1, showing accommodation of a lever arm and utilization for tapping a hole drilled in the bone.

The principles of the apparatus and method of the invention are illustrated, by way of example, with reference to an embodiment of a driver tool 10 (FIG. 1) which can be utilized in accordance with the steps of an embodiment of a method for the tapping or threading of a drilled hole 11 and for the installation of threaded implant components, such as an abutment or screw 12 and an implant base 14, at an implantation site of a patient's mandible or maxilla bone 15 (FIG. 2B and 3).

The tool 10, as shown in FIG. 1, comprises a hand-grippable cylindrical member, in the form of a knurled knob 16, mounted for manual rotation about an axis 18 at one end of an elongated structural element or arm 20. A bit, which may be a tapping bit 19 (FIG. 3) or screw driver bit 21 (FIG. 1), is releasably mounted for rotation about an axis 22 adjacent the other end of the support structure 20. Means is provided for driving the rotation of the bit 19 or 21 directly and positively in response to manual rotation of the knob 16. The tool 10, thus, functions with the bit 21 in the manner of a conventional dental screwdriver or the like, with the knob 16 serving the role of the screwdriver handle and the bit 21 serving the role of the screwdriver shank and head. Unlike the conventional screwdriver, however, the structure 20 serves to laterally offset the axis 18 of rotation of the handle 16 from the axis 22 of rotation of the bit 21. Moreover, whereas with conventional screwdrivers wherein a different screwdriver must be used to match the size and type (allen head or slotted) of the head of the threaded fastener 12, with tool 10 different head sizes and types are accommodated merely by selecting a different one of a plurality of interchangeable bits 21.

To increase the torque advantage of the knob 16 when the tool 10 is used with the bit 19 for tapping or threading the bone hole 11 (FIG. 3), the knob 16 may be provided with an upwardly-opening axial bore 23 for removably receiving the downwardly-directed axial shank 34 of a T-shaped handle 35. The handle 35 has a head 37 with two opposite and outwardly-directed lever arms 38. The shank 34 is keyed to the bore 23, such as by matching rectangular cross-sections, so that rotation of the handle 35 will rotate the knob 16. For tapping different-sized bore holes 11 and different-sized threads to accommodate different sizes of implants 14, a plurality of different-sized tapping bits 19 may be provided. The bits 19 are selectively interchangeable with each other, and with the bits 21.

For the shown embodiment of tool 10, the structural element 20 comprises a lineally extending, thin profile arm having a hollow housing cover portion 24 that matches a planar structural bar 25 (FIG. 1). The bar 25 is fastened over the interior opening of the housing 24 by conventional means, such as screws 26, 27 that thread through housing bores 28, 29 and spacer sleeves 30, 31 into corresponding bores 32, 33. The bores 28, 29 are countersunk and the external surfaces of the housing 24 and bar 25 are rounded to avoid sharp or jagged edges or points that might injure the dentist or patient during the bone tapping or implant installation procedure. All components are stainless steel of surgical quality suitable for heat disinfection and the use of oils or other lubricants is minimized or, if possible, avoided altogether.

The means illustrated in FIG. 1 for directly and positively transmitting torque between the knob 16 and the bit 19 or 21 comprises a drive sprocket 35, a driven sprocket 36 and an unlubricated length of roller chain 38 extending circumferentially about the respective runs of teeth of both sprockets 35, 36. Sprockets 35, 36 are mounted relative to the planar bar 25, so that the rotational axes 18, 22 are generally perpendicular to the plane of the cover and the run of chain is generally parallel thereto. As shown in FIG. 1, sprocket 35 is attached to bar 25 by means of an allenhead screw 39 which projects upwardly through an axial bore 40 of sprocket 35, through the bores of a spacer 41 and an inner race of an X-bearing 42, and into a threaded blind axial bore 43 of a stem of knob 16. Sprocket 36 is attached to the bar 25 by means of an allenhead screw 45 that threads through the axial bores of an inner race of an X-bearing 46 and spacer 47, and into the top of a bore of sprocket 36. The X-bearings 42, 46 are press fitted into bores 48, 49 formed adjacent the respective ends of the bar 25. Slightly larger bores 50, 51 are provided for clearance purposes on corresponding locations adjacent the ends of housing 24. Bores 48, 50 and 49, 51 are formed respectively coaxially with the axes 18, 22. The tool 10 is configured so that the knob 16 projects outwardly adjacent one end on one side of structure 20 (upwardly at left end and top side as seen in FIG. 1) and a bit receiving bore 53 of sprocket 36 is accessible adjacent the opposite end on an opposite side of structure 20 (from below at right end and on the bottom side as seen in FIG. 1).

The bits 19 and 21 have a head end 54 and a shank end 55. For a plurality of interchangeable bits, each head end 54 is differently configured. For example, a set of bits 21 may include several different sized allenheads and several different sized flat heads. A selection of six bits 21 can be made, so that a bit is available to match most commercially available abutments/screws; and bits 19 can be chosen to match commonly available thread sizes of implants 14. The bit shanks 55 are uniformly sized from bit to bit to fit within the bore 53 of sprocket 36. Each shank is configured with a recessed flat portion 57 (segment-shaped in cross-section), intermediate circular cross-sectioned upper and lower remaining portions of the otherwise generally cylindrical shank 55. The shank of a selected bit 19 or 21 is releasably retained within the sprocket bore 53 by means of an allenhead set screw 58 that threads radially against the flat 57. Having larger cross-sectioned portions of shank 55 above and below the flats 57, reduces the risk that a bit 19 or 21 will fall out of the tool 10 during an installation procedure, even though the set screw 58 should become slightly loosened.

To hold an element 12, 14 onto the head 54 of a bit 21 during installation, the invention advantageously provides resilient transparent elastomer sleeves or retainers 60 that have inner bores that may be simultaneously elastically drawn over a bottom portion of shank 55 of bit 21 and a top portion of the head of an element 12, 14. The sleeves 60 are provided in various sizes to match the sizes of the bits 21 and elements 12, 14.

In operation (see FIGS. 1 and 3), a tapping bit 19 is secured within the bore 53 of sprocket 36 of tool 10 by tightening the set screw 58 against the flat portion 57 of the bit shank 55. The bit 19 is chosen to match the threads of the head 54 of the bit 19 with the threads of the chosen implant 14. The axis 22 end of the tool 10 is then inserted into the patient's mouth, with the tapered tip of the head 54 of the bit 19 inserted into the drilled hole 11 at the implantation site of bone 15. The rotary knob 16, located outside the mouth at the axis 18 end of tool 10, is then manually turned by means of the T-shaped handle 35 to rotate the tap 54 to thread the hole 11 for receipt of the implant 14. Following tapping, the axis 22 end of tool 10 is removed from the mouth, the bit 19 is removed and replaced successively by suitable bits 21 for first screwing the implant base 14 into the threaded bone hole 11, and then screwing the screw 12 into the secured base 14.

As shown in FIG. 2A, the top of the head of an element 12, 14 is fitted onto the head 54 of a matching bit 21 of the tool 10 and held in place by the bottom portion of the stretched inside bore of a retainer 60, whose stretched top portion is drawn up onto the shank 55 of the selected bit 21.

The location of the bit end of the structure 10 within the patient's mouth is supported by the fingers of one hand 61 of the user, while the knurled circumferential portion of the knob 16 at the other end of the structure 10 outside the patient's mouth is grasped between the thumb and forefinger of the user's other hand 62. For increased torque, the knob 16 can be turned with the assistance of the "T" handle 35, removably inserted as a lever arm extension into the knob 16. Clockwise rotation of the knurled knob 16 by the thumb and forefinger of the hand 62 (with or without the assistance of the "T" handle 35) will cause corresponding like clockwise rotation of the bit 19 or 21, for tapping the hole 11 or tightening of the threaded element 12, 14. The feeling to the user upon turning the knob 16 will be the same as if the handle of a conventional dental implement directly connected to tap 19 or element 12, 14 were being turned. Rotation of knob 16, rotates sprocket 35 which is connected by means of chain 38 to drive sprocket 36 in like rotational direction. Bit 19 or 21, which is fixed by means of set screw 58 in contact with recess 57, rotates with rotation of sprocket 36.

Unlike conventional ratcheting mechanisms, the elongated arm of structure 20 can be maintained motionless during the installation procedure. As an implant component 12 becomes embedded, the retaining sleeve 60 is pushed back onto the shank 55 of the bit 21, so that it loses its grip on the component, releasing the same. The elasticity of the sleeve 60 is chosen so that it will hold the implant component onto the bit through commencement of installation, but will release the same as installation is completed.

There are, or course, other torque transmission means that can be used to accomplish the same torque transmission function to provide the offset between rotation of the knurled knob 16 and corresponding rotation of the releasably held bit 21. For instance, the knob 16 and bit 21 could each be coupled to bevel gears, which are then respectively coupled to further bevel gears located at the ends of a rotating shaft that extends between the ends of the arm 20.

Figure 4:
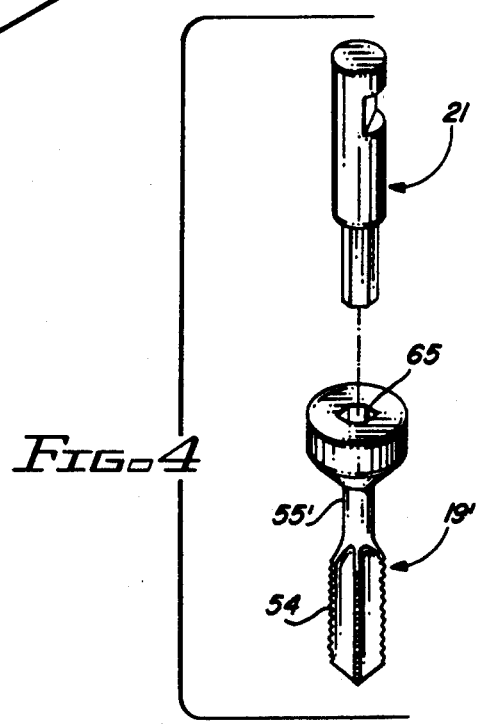
FIG. 4 is a view of a modified form of the tapping bit shown in FIG. 3.

FIG. 4 shows a modified form 19' of tapping bit 19, wherein the head 54 is identical with that of bit 19, but the shank 55' is modified to have a hex opening 65 at its top that complements the hex end of a driver bit 21. Bit 19' is then used in combination, rather than interchangeably, with the bit 21.

Those skilled in the art to which the invention relates will appreciate that other substitutions and modifications can also be made to the described embodiment without departing from the spirit and scope of the invention as described by the claims below.

What is claimed is:

1. A tool for the tapping of a hole in the mandible or maxilla bone of a patient during implant dentistry or the like, comprising:
    an elongated structural element having opposite ends and opposite sides;
    a member rotatably mounted adjacent one end of said element and being hand-grippable from one side of said element for rotation about a first axis transverse to the elongation of said element; said member comprising a knurled knob with a polygonal cross-sectioned, axial opening;
    a tapping bit having a shank portion and a head portion, said head portion being dimensioned, configured and adapted for insertion within the hole of the bone, for tapping the hole when said head portion is rotated;
    means for releasably rotatably securing said bit adjacent the other end of said element for rotation about a second axis parallel to and laterally-spaced in the direction of said elongation from said first axis;
    torque transmission means directly and positively connecting said hand-grippable member and said releasably securing means so that manual rotation of said hand-grippable member causes like rotation of said head portion of said bit secured within said releasably securing means; and
    lever arm means, releasably engageable with said hand-grippable member, for increasing torque manually applied to said hand-grippable member about said first axis; said lever arm means comprising a T-shaped handle having an axial shank with a polygonal cross-section matching and insertable within said cross-section of said member opening, and a head with two opposite and outwardly-directed lever arms.

2. A tool as in claim 1, further comprising a device bit having a shank portion with a polygonal cross-sectioned end; and wherein said tapping bit shank portion is formed with a polygonal cross-sectioned opening that complements the polygonal cross-sectioned end of the driver bit.

3. A method for the tapping of a hole in the mandible or maxilla bone at an implant site within the mouth of a patient during implant dentistry or the like, said method comprising the steps of:
    providing a dental tool having an elongated arm with opposite ends and opposite sides; a hand-grippable member rotatably mounted adjacent one end on said arm; a tapping bit rotatably mounted adjacent said other end on said arm, said tapping bit including a head portion; and torque transmission means connecting said hand-grippable member and said tapping bit, so that rotation of said hand-grippable member causes like rotation of said bit;
    placing said arm with said one end located outside of the patient's mouth and with said other end located within the patient's mouth, said head portion of said tapping bit engaging the hole in the bone at the implant site; and
    tapping the bone hole by manually rotating said hand-grippable member to rotate said tapping bit, so that threads are formed on the interior of the bone hole.

4. A method as in claim 3, for the tapping of the bone hole and the subsequent installation of an implant element in the tapped hole, wherein said providing step further comprises providing a screwing bit interchangeable with said tapping bit, said screwing bit including a head portion dimensioned, configured and adapted to mate with said threaded implant element; and said method further comprises the steps of:
    rotatably mounting said screwing bit adjacent said other end of said arm in place of said tapping bit;
    positioning the implant element at the site of the tapped bone hole within the mouth of the patient;
    placing said arm with said one end located outside of the patient's mouth and with the other end located within the patient's mouth, said head portion of said screwing bit in mating engagement with the implant element positioned at said tapped bone hole site; and screwing the implant element into said tapped bone hole by manually rotating said hand-grippable member to rotate said screwing bit, so that the implant element is threaded into said bone hole threads formed by said tapping step.

5. A method as in claim 4, wherein said providing step further comprises providing a resilient elastomer sleeve having an internal bore, and said implant element positioning step comprises stretching said internal bore over said screwing bit and over the implant element to hold said head portion of said screwing bit in mating engagement with the implant element.

6. A method as in claim 3, wherein said providing step further comprises providing a lever arm member dimensioned, configured and adapted for selective engagement with said hand-grippable member; and wherein in said tapping step, the bone hole is tapped by engaging said lever arm member with said hand-grippable member, and manually rotating said lever arm member.

7. A method as in claim 6, wherein said hand-grippable member has an axial opening, said lever arm member comprises a T-shaped handle having an axial shank and a head with two opposite and outwardly-directed lever arms, and said hole is tapped by inserting said axial shank within said axial opening, and manually rotating said lever arms.

8. A method for the tapping of a hole in the mandible or maxilla bone at an implant site within the mouth of a patient during implant dentistry or the like, said method comprising the steps of:

providing a dental tool having an elongated arm with opposite ends and opposite generally planar parallel sides; a knurled knob; a first sprocket attached to said knurled knob; means mounting said knob on one of said sides adjacent one of said ends for rotation about a first axis perpendicular to said parallel sides; a tapping bit, including a head portion dimensioned, configured and adapted for insertion within the hole of the bone; a screwing bit, including a head portion dimensioned, configured and adapted to mate with the implant element; a second sprocket; means for releasably attaching a selected one of said tapping and screwing bits to said second sprocket; means mounting said second sprocket on the other of said ends for rotation of said selectively attached bit about a second axis parallel to and laterally-spaced in the direction of elongation of said arm from said first axis; and a roller chain connecting said first and second sprockets, so that rotation of said knob will cause rotation of said selectively attached bit;

attaching said tapping bit to said second sprocket using said attaching means;

placing said arm with said one end located outside of the patient's mouth and with said other end located within the patient's mouth, said head portion of said tapping bit engaging the hole at the implant site;

tapping the bone hole by manually rotating said knurled knob to rotate said tapping bit, so that threads are formed on the interior of the bone hole;

attaching said screwing bit to said second sprocket in place of said tapping bit, using said attaching means;

providing a resilient elastomer sleeve having an internal bore;

stretching said internal bore over said screwing bit and over the implant element to hold said head portion of said screwing bit in mating engagement with the implant element;

positioning the implant element held by said sleeve at the implant site within the mouth of a patient, with said arm positioned so that said one end is located outside of the patient's mouth and said other end is located within the patient's mouth;

manually rotating said knob, to rotate said screwing bit; thereby rotating the implant element into an installed position within the tapped bone hole;

releasing said sleeve from the implant element; and withdrawing the tool and sleeve attached to the screwing bit out of the patient's mouth.

* * * * *